(12) United States Patent
Suehira et al.

(10) Patent No.: US 9,055,891 B2
(45) Date of Patent: Jun. 16, 2015

(54) OPTICAL TOMOGRAPHIC IMAGE PHOTOGRAPHING APPARATUS AND CONTROL METHOD THEREFOR

(75) Inventors: Nobuhito Suehira, Kawasaki (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 108 days.

(21) Appl. No.: 13/405,678

(22) Filed: Feb. 27, 2012

(65) Prior Publication Data

US 2012/0229763 A1    Sep. 13, 2012

(30) Foreign Application Priority Data

Mar. 10, 2011 (JP) ................................ 2011-052292

(51) Int. Cl.
| | |
|---|---|
| A61B 3/14 | (2006.01) |
| A61B 3/10 | (2006.01) |
| G01B 9/02 | (2006.01) |
| G06T 7/20 | (2006.01) |

(52) U.S. Cl.
CPC ............ *A61B 3/102* (2013.01); *G01B 9/02091* (2013.01); *G06T 7/2033* (2013.01); *G01B 9/0203* (2013.01); *G01B 9/02077* (2013.01); *G06T 2207/10101* (2013.01); *G06T 2207/30041* (2013.01)

(58) Field of Classification Search
USPC .................. 351/200, 205–206, 209–221, 246
See application file for complete search history.

(56) References Cited

U.S. PATENT DOCUMENTS

| | | |
|---|---|---|
| 6,325,512 B1 | 12/2001 | Wei |
| 7,452,077 B2 | 11/2008 | Meyer et al. |
| 7,643,154 B2 | 1/2010 | Kikawa et al. |
| 2005/0270486 A1 | 12/2005 | Teiwes et al. |

(Continued)

FOREIGN PATENT DOCUMENTS

| | | |
|---|---|---|
| CN | 101234015 A | 8/2008 |
| CN | 102232824 A | 11/2011 |

(Continued)

OTHER PUBLICATIONS

Jun. 21, 2012 European Search Report in European Patent Appln. No. 12158529.3.

(Continued)

*Primary Examiner* — Scott J Sugarman
*Assistant Examiner* — Robert E Tallman
(74) *Attorney, Agent, or Firm* — Fitzpatrick, Cella, Harper & Scinto (57) ABSTRACT

An optical tomographic image photographing apparatus having a tracking function, capable of appropriately controlling a scan in acquiring a tomographic image. The optical tomographic image photographing apparatus according to the invention includes a fundus image photographing section which photographs fundus images of an eye to be inspected and a tomographic image photographing section which photographs tomographic images of the eye to be inspected. A control method of the optical tomographic image photographing apparatus includes the steps of: calculating coordinate values matching a plurality of previously-acquired characteristic areas in the fundus image; calculating a spatial variation between the plurality of coordinate values; and controlling the scan of a measuring light by the tomographic image photographing section for acquiring the tomographic images on the basis of a result of the calculation.

32 Claims, 4 Drawing Sheets

(56) References Cited

U.S. PATENT DOCUMENTS

| | | |
|---|---|---|
| 2008/0055543 A1 | 3/2008 | Meyer et al. |
| 2008/0151256 A1 | 6/2008 | Kikawa et al. |
| 2009/0115964 A1 | 5/2009 | Ueno |
| 2010/0110171 A1 | 5/2010 | Satake |
| 2010/0226553 A1 | 9/2010 | Suehira |
| 2010/0226554 A1 | 9/2010 | Suehira |
| 2010/0315590 A1 | 12/2010 | Ueno |
| 2011/0058175 A1 | 3/2011 | Suehira |
| 2011/0096333 A1 | 4/2011 | Suehira et al. |
| 2011/0098560 A1 | 4/2011 | Suehira et al. |
| 2011/0103655 A1* | 5/2011 | Young et al. ............. 382/128 |
| 2011/0267580 A1* | 11/2011 | Nakajima et al. ......... 351/206 |
| 2011/0299035 A1 | 12/2011 | Suehira |
| 2011/0299037 A1 | 12/2011 | Ueno |
| 2012/0002166 A1 | 1/2012 | Tomatsu et al. |
| 2012/0044499 A1 | 2/2012 | Shimoyama et al. |
| 2013/0093997 A1 | 4/2013 | Utsunomiya et al. |

FOREIGN PATENT DOCUMENTS

| | | |
|---|---|---|
| CN | 102970919 A | 3/2013 |
| EP | 2 184 004 A1 | 5/2010 |
| EP | 2 322 081 A1 | 5/2011 |
| EP | 2 382 913 A1 | 11/2011 |
| JP | 2004-512125 A | 4/2004 |
| JP | 2010-012109 A | 1/2010 |
| JP | 2010-110392 A | 5/2010 |
| JP | 2010-227610 A | 10/2010 |
| JP | 2011-019576 A | 2/2011 |
| JP | 2011-098221 A | 5/2011 |
| WO | 02/35996 A1 | 5/2002 |
| WO | 2011/007632 A1 | 1/2011 |
| WO | 2012/002406 A1 | 1/2012 |

OTHER PUBLICATIONS

Mar. 24, 2014 Chinese Official Action in Chinese Patent Appln. No. 201210064119.6.

Apr. 9, 2015 Chinese Official Action in Chinese Patent Appln. No. 201210064119.6.

* cited by examiner

OPTICAL TOMOGRAPHIC IMAGE PHOTOGRAPHING APPARATUS AND CONTROL METHOD THEREFOR

BACKGROUND OF THE INVENTION

1. Field of the Invention

The present invention relates to an optical tomographic image photographing apparatus and a control method therefor.

2. Description of the Related Art

In recent years, an optical coherence tomography (OCT) device, which is capable of acquiring a tomographic image of a fundus, has received attention. One of the reasons therefor is the OCT device enables a noninvasive and high-resolution observation of the tomographic structure of a fundus. Particularly, SD-OCT (spectral domain) devices capable of high-speed and high-sensitive measurement occupy a central position in the market. These SD-OCT devices are increasingly sophisticated by being provided with a fundus camera or a scanning laser ophthalmoscope (SLO).

On the other hand, in order to detect a tiny tumor or other abnormalities by early diagnosis and early treatment, an increase in the image quality of tomographic image is demanded. As a unit for achieving high image quality, there is disclosed a device for causing an OCT beam to follow the movement of an eyeball (Japanese Unexamined Patent Application Publication [Translation of PCT Application] No. 2004-512125). In the invention disclosed in Japanese Unexamined Patent Application Publication (Translation of PCT Application) No. 2004-512125, an OCT device is provided with a device for detecting the movement of an eyeball. It is described that the device tracks an optic papilla of a fundus and controls a tracking scanner in real time to facilitate the acquisition of a tomographic image at a desired place.

There are, however, various movements of an eyeball and can be classified into the following: a micro saccade, which is a fast and linear movement; a drift, which is a slightly slow movement; and a tremor, which is a fast vibration with a small amplitude occurring during drifting. While the moving speed and frequency of the movement depend on each individual, the micro saccade is said to have a speed in the order of several mm/sec, which is an incommensurable speed compared to the drift having a speed in the order of 100 μm/sec. The cycle of the micro saccade is in the order of once or twice per several seconds. The drift continues to move without a break. The tremor is a small movement with an amplitude of 5 μm, though having a cycle in the order of 100 Hz.

Among them, the micro saccade sometimes occurs within the time for photographing a fundus image when detecting the movement of an eyeball by using a fundus image. Moving a scanner on the basis of the fundus image at the time of occurrence of this phenomenon causes the scanner to be moved to an unexpected position. Therefore, it is necessary to detect a sudden eye movement on the basis of the fundus image to prevent such a situation.

SUMMARY OF THE INVENTION

It is an object of the present invention to execute a measuring light scan appropriately in an apparatus which causes a measuring light to follow the movement of an object to be inspected in acquiring a tomographic image.

In order to solve the above object, according to the present invention, there is provided a control method of a photographing apparatus for acquiring first and second fundus images of an eye to be inspected at different time points, the method including the steps of: extracting a plurality of characteristic images from the first fundus image; searching the plurality of characteristic images extracted from the second fundus image; and determining whether there is a spatial variation between a positional relation of the plurality of extracted characteristic images and a positional relation of the plurality of searched characteristic images.

Moreover, to solve the above problem, according to the present invention, there is provided a tomographic image photographing apparatus including: a fundus image photographing section which acquires first and second fundus images of an eye to be inspected at different time points; an extraction unit which extracts a plurality of characteristic images from the first fundus image; a search unit which searches the plurality of characteristic images extracted from the second fundus image; and a determination unit which determines whether there is a spatial variation between a positional relation of the plurality of extracted characteristic images and a positional relation of the plurality of searched characteristic images.

According to the present invention, an appropriate scan control is achieved when acquiring a tomographic image.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

Hereinafter, a first embodiment of the present invention will be described. A photographing apparatus in this embodiment has an internal fixation lamp, uses an SLO photographing section to acquire a fundus image, calculates a moving amount of an eyeball from the fundus image acquired using the SLO photographing section, and reflects a result of the calculation on an OCT photographing section to acquire a tomographic image.

(Structure of OCT Photographing Section)

Figure 1:
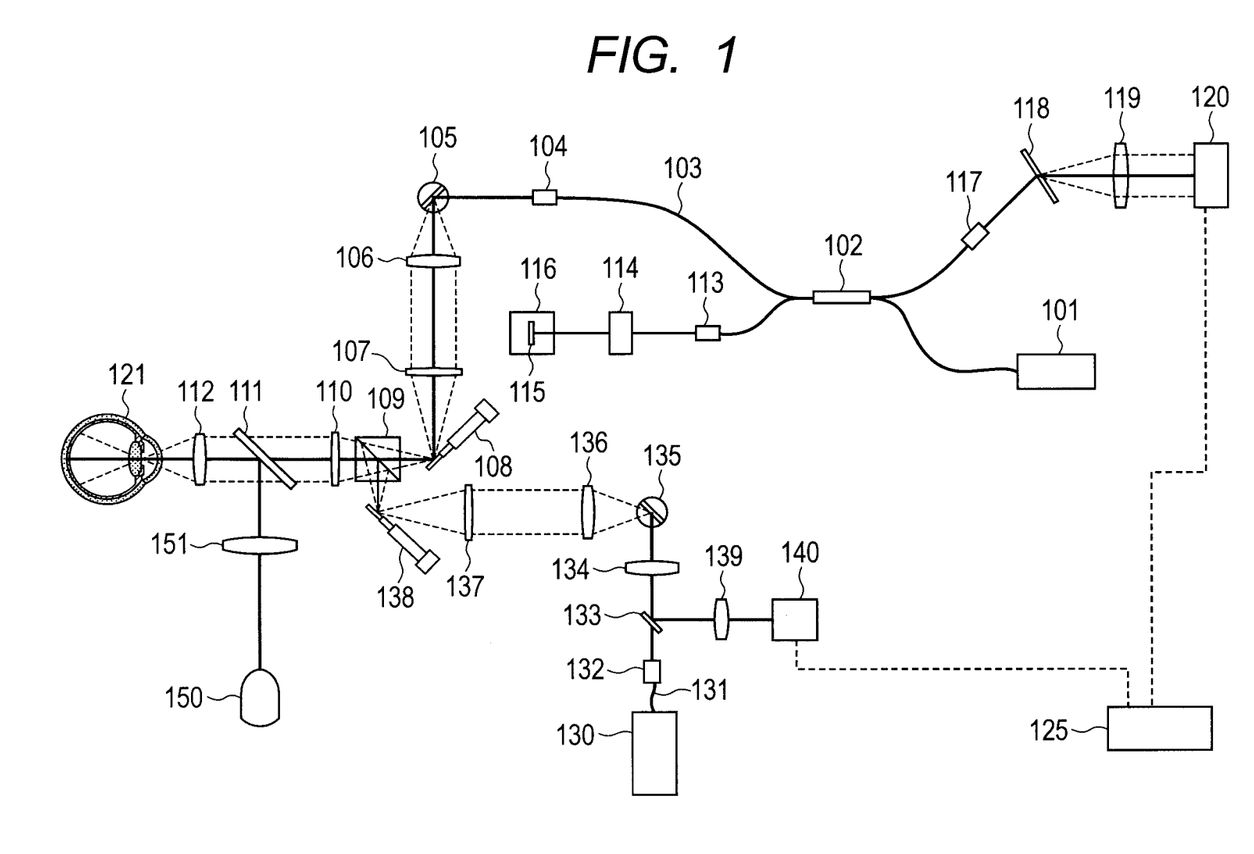
FIG. 1 is a schematic diagram of an optical system structure of an optical tomographic image photographing apparatus in a first embodiment of the present invention.

FIG. 1 is a schematic diagram of an optical system structure of the photographing apparatus in this embodiment. A low-coherent light source 101 is used as a light source. As the light source 101, a super luminescent diode (SLD) light source or an amplified spontaneous emission (ASE) light source can be used. For a low-coherent light, wavelengths at 850 nm and its vicinity and at 1,050 nm and its vicinity are used for photographing a fundus of an eye. In this embodiment, an SLD light source having a center wavelength of 840 nm and a full-width at half-maximum of 45 nm is used.

The low coherent light emitted from the low coherent light source 101 enters a fiber coupler 102 via a fiber and is split into a measuring light (OCT beam) and a reference light. Although a structure of an interferometer using a fiber is described here, a structure using a beam splitter in a spatial light optical system may be adopted.

The measuring light is emitted in the form of a parallel light from a fiber collimator 104 via a fiber 103. The emitted measuring light further passes through an OCT scanner (Y) 108 via an OCT scanner (X) 105 and relay lenses 106 and 107, and passes through a dichroic beam splitter 109, a scan lens 110, a dichroic mirror 111, and an ocular lens 112, so as to irradiate an eye to be inspected 121. Here, as the OCT scanners (X) 108 and (Y) 105, galvano scanners are used. The measuring light in the eye to be inspected 121 is scattered and reflected by a retina and traces the same optical path to return to the fiber coupler 102 as a return light.

The reference light is guided to a fiber collimator 113 from the fiber coupler 102 and emitted in the form of a parallel light. The emitted reference light passes through a dispersion compensating glass 114 and is reflected by a reference mirror 116 on an optical path length variable stage 115. The reference light reflected by the reference mirror 116 traces the same optical path to return to the fiber coupler 102.

The return light and the reference light that have returned are combined to be a combined light in the fiber coupler 102 and guided to a fiber collimator 117. The combined light is converted to intensity information of each wavelength by a spectroscope and then measured. The fiber collimator 117, a grating 118, a lens 119, and a linear sensor 120 constitute the spectroscope. The intensity information of each wavelength measured by the linear sensor 120 is transmitted to a PC 125 and is generated as a tomographic image of the eye to be inspected.

In the OCT measurement, a fixation lamp 150 is used to make stable the fixation. For the fixation lamp 150, light-emitting diodes (LEDs) arranged in a matrix are used. The position of an illuminated LED is varied, in accordance with a site desired to be photographed, by the control of the PC 125. The light from the LEDs has a wavelength of 500 nm. The beam emitted from the fixation lamp irradiates the eye to be inspected 121 via a lens 151 and the dichroic mirror 111. The dichroic mirror 111 is disposed between the scan lens 110 and the ocular lens 112 to separate a light having a short wavelength (in the order of 500 nm) from the OCT beam and SLO beam (700 nm or greater).

(Structure of SLO Photographing Section)

Subsequently, an optical system structure of an SLO photographing section for acquiring a fundus image is described. As a laser light source 130, a semiconductor laser or an SLD light source can be used. A wavelength to be used in the light source is not limited as long as it can be separated from a wavelength of the low coherent light source 101 for OCT by the dichroic beam splitter 109. Generally, a near-infrared wavelength range of 700 to 1,000 nm, which is preferable for the image quality of a fundus image, is used. In this embodiment, a semiconductor laser having a wavelength of 760 nm, by which the light can be separated, is used.

The laser beam (SLO beam) emitted from the laser light source 130 is emitted in the form of a parallel light from a fiber collimator 132 via a fiber 131 and is guided to an SLO scanner (Y) 135 via a ring mirror 133 and a lens 134. The laser beam passes through an SLO scanner (X) 138 via lenses 136 and 137 and is reflected by the dichroic beam splitter 109 to enter the eye to be inspected 121 as a target. The dichroic beam splitter 109 is adapted to transmit an OCT beam and to reflect an SLO beam. Similarly to the OCT photographing section, a galvano scanner is used as a scanner of the SLO photographing section. The SLO beam entering the eye to be inspected 121 irradiates the fundus of the eye to be inspected 121. This beam is reflected or scattered by the fundus of the eye to be inspected 121 and traces the same optical path so as to return to the ring mirror 133. The ring mirror 133 is disposed at a position that is conjugate with the position of a pupil of the eye to be inspected 121. Out of the back-scattered light of the beam irradiating the fundus, light passing through a periphery of the pupil is reflected by the ring mirror 133 and forms an image on a light detection element 140 by a lens 139. The light detection element 140 is, for example, an avalanche photodiode (APD). A plane image of the fundus is generated on the basis of the intensity information of the light detection element 140. Although an SLO for acquiring a fundus image by irradiating the fundus with the beam having a spot diameter and scanning is used in this embodiment, a line SLO (LSL) structure using a line beam may be adopted.

The PC 125 not only controls the OCT scanner, the optical path length variable stage 115, the linear sensor 120, the SLO scanner, the light detection element 140, and the fixation lamp 150 and acquires data, but also executes signal processing and the fetch or storage of data.

(Signal Processing)

Figure 2:
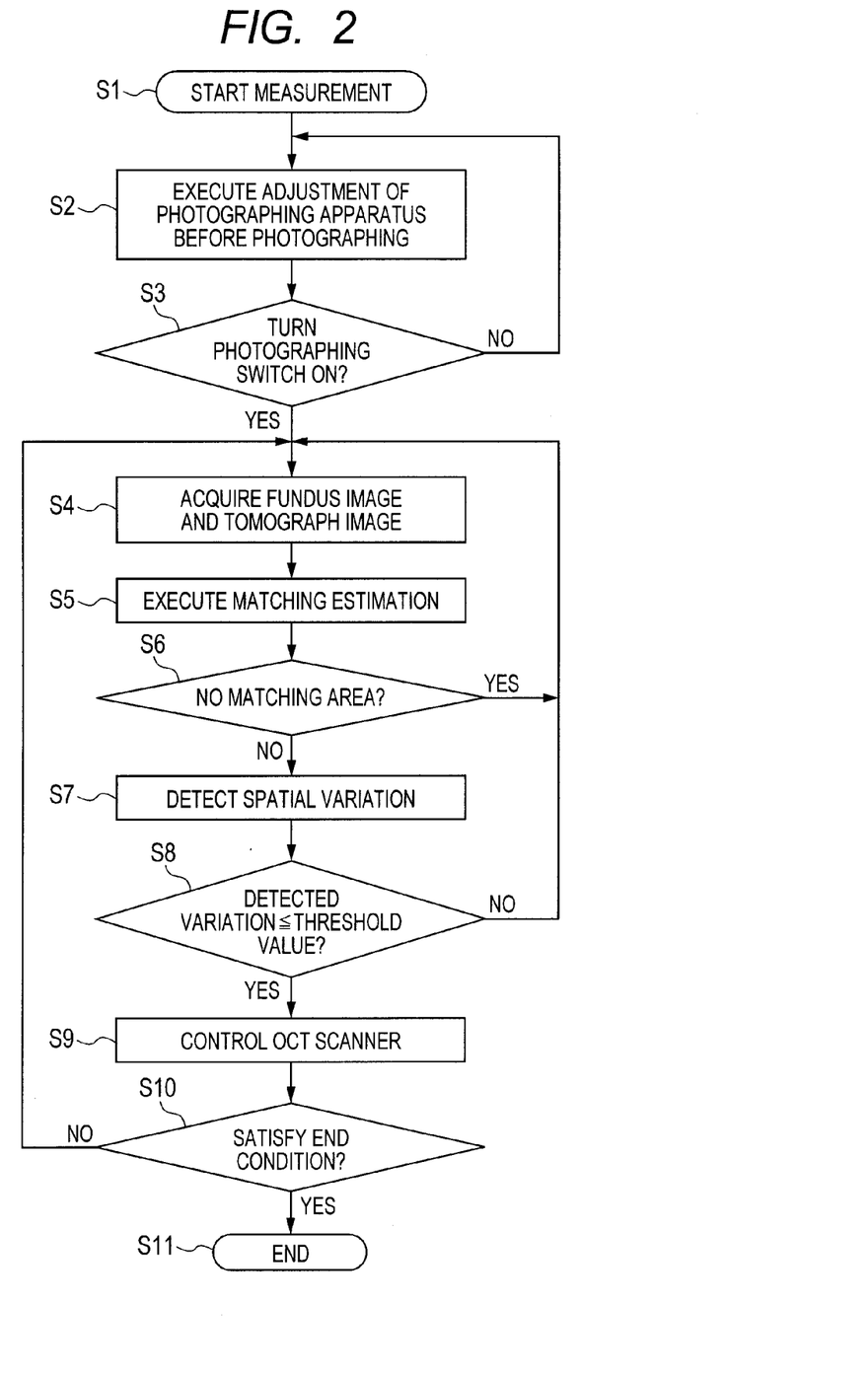
FIG. 2 is a flowchart of signal processing in the first embodiment of the present invention.

Signal processing is described below with reference to the flowchart of FIG. 2. The description is made for a case where the SLO photographing section and the OCT photographing section have the same frame rate in this embodiment. The SLO photographing section and the OCT photographing section execute photographing almost at the same timing. The photographing position in photographing a tomographic image using the OCT photographing section is controlled on the basis of the fundus image from the SLO photographing section.

In step S1, measurement is started. In this state, the photographing apparatus has already been started and the eye to be inspected 121 has been disposed in a measurement position. In addition, a mode for photographing using the OCT photographing section is selected. The mode includes a measurement range, a measurement position, and a repeat count. In this embodiment, description is made by giving an example of a mode for photographing the same place on a retina 50 times.

In step S2, adjustment of the photographing apparatus before photographing is executed for a fundus image and a tomographic image. It is necessary to execute alignment of the photographing apparatus and the eye to be inspected before photographing the tomographic image. While watching the fundus image acquired by the SLO photographing section, the adjustment is executed for a distance between the eye to be inspected 121 and the photographing apparatus (particularly an optical system) and for the position of the scan lens 110 so that the fundus image is clearly visible. Subsequently, the illuminated position of the fixation lamp is moved so that a desired area is able to be measured. Further, the optical path length variable stage 115 is adjusted so as to include the range necessary for photographing the tomographic image using the OCT photographing section. In this step, a plurality of characteristic areas are extracted from the fundus image acquired by the SLO photographing section and then stored as templates. Although description is made for a case of extracting four areas here, the number of areas is not limited as long as two or more areas are extracted. As described later, in the case of executing pattern matching with the fundus image divided into four quadrants, it is preferable to extract characteristic areas from quadrants diagonally opposite to each other. In order to detect a micro saccade preferably in this state, it is more preferable to extract a characteristic area from other quadrants to use three or more characteristic areas. Although increasing the number of extracted areas increases the possibility of accurately detecting a rapid movement such as a micro saccade, it leads to an increase in calculation time. The above step of extracting the characteristic images is executed in an area which functions as an extraction unit of the PC 125 in the present invention.

Figure 3A:
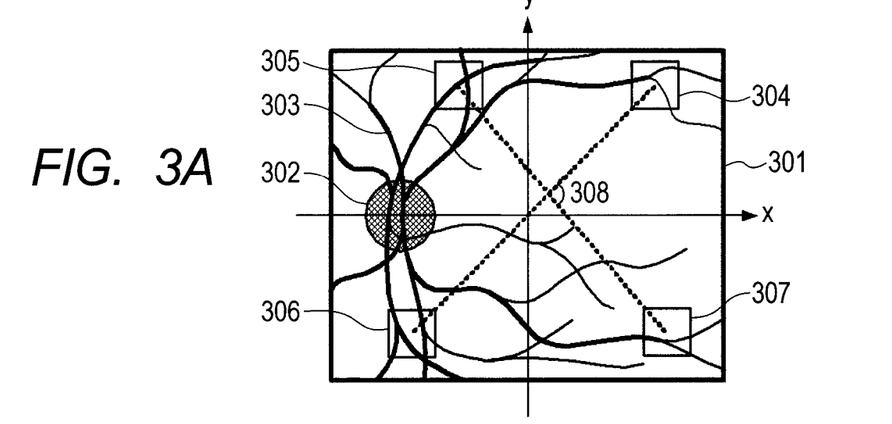
FIGS. 3A, 3B and 3C are diagrams for describing pattern matching in the first embodiment of the present invention, respectively.

Here, the extraction of the characteristic areas is described with reference to FIGS. 3A to 3C. The fundus image is assumed to have dimensions of 600 pixels high and 800 pixels wide. Scanning by the scanner starts from the top left of FIG. 3A and the y axis is moved by one step every time the scanner reciprocates on the x axis to execute measurement up to the bottom right. The x axis is in a so-called "fast scan" direction and the y axis is in a so-called "slow scan" direction. A fundus image 301 in FIG. 3A, which is a first fundus image, includes a papilla 302 and a blood vessel 303. The acquired fundus image is divided into four quadrants, first to fourth quadrants, the x and y axes with the center as the origin. In addition, the characteristic areas are extracted from the quadrants, respectively, such as one characteristic area from each quadrant. Although the characteristic areas are described taking an example of a branch of a blood vessel, naturally the characteristic may be any other characteristic such as a papilla. The characteristic area has dimensions such as, for example, 50×50 pixels. The first to fourth quadrants are areas indicated by 304 to 307, respectively. The characteristic areas are stored as templates and then the processing proceeds to step S3.

In step S3, it is determined whether a photographing switch is turned on. If the photographing switch is turned on, the processing proceeds to step S4 to start photographing a tomographic image. Otherwise, the processing returns to the adjustment of the photographing apparatus before photographing in step S2 to execute the adjustment before photographing and the extraction of templates.

In step S4, the fundus image and the tomographic image are acquired. First, the fundus image is acquired by the SLO photographing section. The SLO scanner (X) 138 provides a fast scan and the SLO scanner (Y) 135 provides a slow scan, by which a two-dimensional fundus image in an xy plane is acquired. The fundus image is assumed to have 800 pixels in the x direction and 600 pixels in the y direction.

On the other hand, the tomographic image is acquired by the OCT photographing section. The OCT scanner (X) 108 provides a fast scan with reciprocating on the x axis and the OCT scanner (Y) 105 maintains a fixed value on the y axis. As a result, a two-dimensional tomographic image in an xz plane is acquired. Note that 1,000 lines are acquired as an output from the spectroscope by photographing an image once. In signal processing, the output of the spectroscope is made at equal intervals with respect to a wavelength and therefore is converted so as to be made at equal intervals with respect to a wave number. Subsequently, a Fourier transform is executed. A necessary part is cut out, by which a tomographic image in the xz plane (1,000 pixels in the x direction and 500 pixels in the z direction) is acquired.

In step S5, pattern matching is executed for a plurality of templates. First, processing of pattern matching is executed between the fundus image acquired as the second fundus image and the template of each quadrant. For the pattern matching, a general method may be adopted, and therefore the details thereof are not described here. As the coordinates of a matching detection area for each quadrant, the central coordinates $(x_i(t), y_i(t))$ of the area are output, where i is an integer from 1 to 4, which indicates each of the four quadrants, and t is time after the template is extracted. In this manner, whether there is a detection area matching the template and the number of the detection areas are detected by pattern matching. If there is no matching area, an error is output. In this process, as described later, it is also possible to determine the matching by determining whether a distance between the four templates or a spatial variation calculated from an angle between diagonal lines satisfies a predetermined condition (for example, whether it is a predetermined value or more). In the case of an error, the fundus image does not match any of the templates or does not match one template, for example. In this embodiment, a state where the image does not match one or more templates is considered to be an error. In the present invention, the aforementioned step of detecting a detection area is executed by an area which functions as a search unit for executing the step of searching the detection areas, i.e., search areas corresponding to the aforementioned characteristic images in the PC 125.

In addition, an occurrence of an error may be displayed so that an inspector is able to warn a subject not to move by means of an alarm display or the like. Moreover, preferably an occurrence of an error is determined from a shift of the central coordinates relative to a predetermined value, which is found by, for example, the number of pixels obtained by multiplying a predetermined scaling factor by each of the number of pixels in the vertical direction and the number of pixels in the horizontal direction of the characteristic area or the number of pixels obtained by adding a predetermined number of pixels to each.

In step S6, it is determined whether there is no matching area. If there is a matching area, the processing proceeds to step S7. If there is no matching area, the processing returns to step S4. If there is a matching area (FIG. 3B), a tracking operation is executed on the basis of the first and second fundus images. Moreover, if there is no matching area (FIG. 3C), a third fundus image is acquired and a tracking operation is executed on the basis of the first and third fundus images. In other words, if there is no matching area, the second fundus image is not used for the tracking operation. No matching area occurs in the case where there is no part matching the template in the fundus image because the eye moves, in the case where a micro saccade occurs during photographing the characteristic area extracted as a template, and in the case where the eye is closed. In the image where the error occurs, the tomographic image acquired at the same time as the image is likely to be an inappropriate image similarly, and therefore the tomographic image is not included in the number of acquired images. In other words, if the calculated spatial variation is equal to or greater than a predetermined value, the tomographic image acquired at the same time as the fundus image when acquiring the detection area used to detect matching with the characteristic area is discarded. Specifically, the fundus image having a spatial variation equal to or greater than the predetermined value is not used for the tracking operation, but the tracking operation is executed by using a fundus image having a spatial variation smaller than the predetermined value. The spatial variation described here corresponds to a variation caused by a movement or a distortion in the layout of the image within a space where there is a retina including the acquired fundus image or tomographic image, in other words, corresponds to a spatial variation in each positional relation of the characteristic images. The above discarding is executed by an area functioning as a discarding unit in the PC 125 in the present invention. Moreover, while it is determined whether there is a spatial variation on the basis of the positional relation between the extracted characteristic images and the searched characteristic images, which have already been extracted, this step is executed by an area functioning as a determination unit in the PC 125.

In step S7, a spatial variation between matching coordinate values is detected and the magnitude of the variation is calculated by using the mathematical expression described below. The spatial variation is detected as a variation in the distance between the detection areas selected as areas matching the characteristic areas and in the angle formed by an intersection of line segments obtained by connecting the detection areas as a pair (the angle between the line segments). First, the distance is assumed to be a distance between the matching detection areas in the respective quadrants. For example, the distance between matching coordinate values of a quadrant i and a quadrant j is expressed by the following mathematical expression 1:

$$r_{ij}(t) = \sqrt{(x_i(t)-x_j(t))^2+(y_i(t)-y_j(t))^2}$$ Mathematical Expression 1

In the case of using four templates, the length of a diagonal line of a rectangle formed by the templates is longer than a side of the rectangle. Further, the acquisition time varies in the Y direction. Therefore, $r_{13}(t)$ for the diagonal line of the first quadrant and the third quadrant is used here. Naturally, the diagonal line of the second quadrant and the fourth quadrant may be used, both diagonal lines may be used, and a diagonal line longer in distance may be used. Generally, either one can be used for detection in the case of a micro saccade. Here, the distance variation is expressed by the following mathematical expression 2:

$$\Delta r_{13}(t) = r_{13}(t) - r_{13}(0)$$ Mathematical Expression 2

Subsequently, a vector connecting the matching detection areas in the quadrant i and the quadrant j is expressed by the following mathematical expression 3:

$$\vec{a_{ij}(t)} = (x_j(t)-x_i(t), y_j(t)-y_i(t))$$ Mathematical Expression 3

An angle θ 308 between diagonal lines connecting the detection areas in the first and third quadrants and in the second and fourth quadrants, respectively, is expressed by the following mathematical expression 4:

$$\theta(t) = \cos^{-1}\frac{\vec{a_{31}(t)} \cdot \vec{a_{24}(t)}}{|\vec{a_{31}(t)}||\vec{a_{24}(t)}|}$$ Mathematical Expression 4

Therefore, the variation in the angle θ between the diagonal lines is expressed by the following mathematical expression 5:

$$\Delta\theta(t) = \theta(t) - \theta(0)$$ Mathematical Expression 5

In step S8, the detected variation is compared with a threshold value. The comparison with the threshold value is executed for each of the distance and the angle, as expressed by the following mathematical expressions 6-1 and 6-2:

$$\Delta r_{13}(t) \leq R_{13}$$ Mathematical Expression 6-1

$$\Delta\theta(t) \leq T$$ Mathematical Expression 6-2

As described hereinabove, the spatial variation is calculated as a variation in the distance between detection areas selected out of the plurality of detection areas or a variation in the angle between two line segments connecting the selected detection areas. Moreover, in this case, preferably the plurality of characteristic areas are four or more areas and the spatial variation is calculated as a variation in the distance between at least one pair of detection areas. Alternatively, preferably the plurality of characteristic areas are four or more areas and the spatial variation is calculated as a variation in the angle between two diagonal lines connecting detection areas diagonally opposite to each other in the fundus image.

Figure 3B:
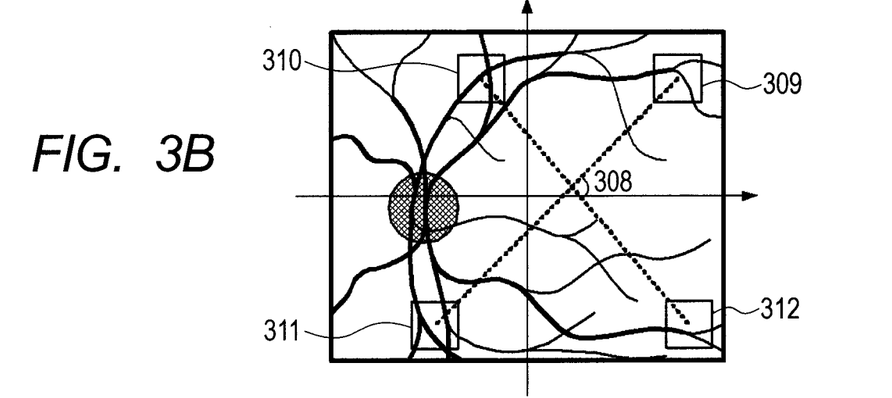
Figure 3C:
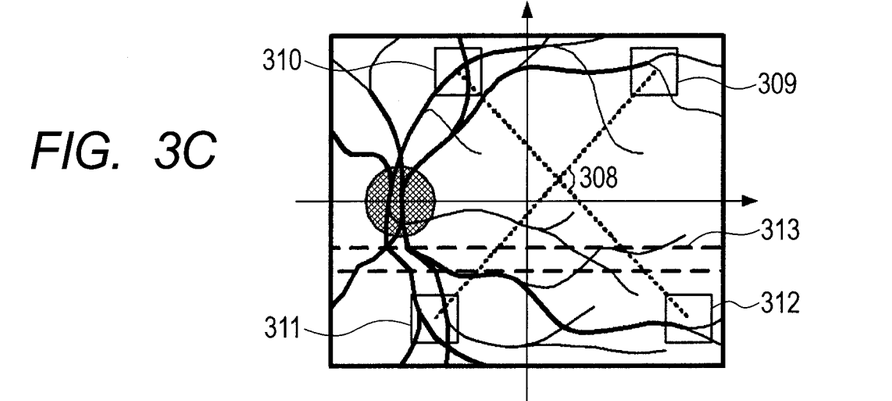

Here, description is made for a case where the eye drifts with reference to FIG. 3B. The matching detection areas are as indicated by 309 to 312 in the first to fourth quadrants in order. In the case of drift, the fundus image wholly moves in parallel or rotationally moves. Therefore, no variation occurs in the distance between matching detection areas and an angle between diagonal lines. In this case, the processing proceeds to step S9. On the other hand, description is made for a case where a micro saccade has occurred in an area 313 indicated by dashed lines as illustrated in FIG. 3C. A blood vessel is as if it were unnaturally drawn-out. In this state, the distance between the matching coordinate values and the angle 308 between the two diagonal lines are different from the initial values, which do not satisfy the mathematical expressions 6-1 and 6-2. The compared value is, for example, several percent of the value at t=0 in the mathematical expressions 1 and 4.

Unless this condition is satisfied, the eye has already moved to a position different from the coordinates of the matching detection areas of the first quadrant 304 and the second quadrant 305. Therefore, it is unlikely to be able to photograph a desired place even if the scanner is controlled by using this fundus image. The processing returns to step S4 to acquire the fundus image again to check the position of the eye. It is, however, likely to be able to acquire a desired area as long as a moving amount is calculated by using the third quadrant 306 and the fourth quadrant 307. Specifically, if the spatial variation in the characteristic image satisfies a predetermined condition, i.e., a condition of a value equal to or smaller than the threshold value in this embodiment, a tracking operation is executed on the basis of the first fundus image and the second fundus image for which the above matching operation is executed. Otherwise, another fundus image, namely the third fundus image in this embodiment is acquired and then a tracking operation is executed using the fundus image.

In step S9, the scan mode (the scan start position, scan range, etc.) of the OCT scanner is controlled to correct an acquired tomographic image. The OCT scanner is controlled by calculating the moving amount of the OCT scanner, first. Here, it is assumed to be a variation amount relative to the center of gravity of the four detection areas. Assuming that the center of gravity of the four areas matching the templates is $(x_m(t), y_m(t))$, the relation is expressed by the following mathematical expression 7:

$$(x_m(t), y_m(t)) = \left(\frac{x_1(t)+x_2(t)+x_3(t)+x_4(t)}{4}, \frac{y_1(t)+y_2(t)+y_3(t)+y_4(t)}{4}\right)$$ Mathematical Expression 7

Therefore, the moving amount of the detection area relative to the extraction area is expressed by the following mathematical expression 8:

$$\Delta x_m(t), \Delta y_m(t)) = (x_m(t)-x_m(0), y_m(t)-y_m(0))$$ Mathematical Expression 8

After calculating the moving amount, the OCT scanner is controlled. The OCT scanner is controlled by varying offset amounts in the x and y directions. In other words, the spatial variation can be calculated with the moving amount of the detection areas relative to the characteristic areas as the movement of the center of gravity of the detection areas.

In step S10, it is determined whether the end condition is satisfied. The end condition is that a required number of images (50 sheets) are completed to be photographed or that a preset predetermined time (for example, two minutes) has elapsed after the measurement is started, and in this case, an error is output and the processing is terminated. Unless the end condition is satisfied, the processing returns to step S4 to execute photographing. The processing from step S4 to step S10 takes, for example, on the order of 40 msec for one-time processing. In other words, it takes two seconds as long as 50 sheets of images are able to be photographed continuously.

In step S11, the processing ends. After the end of the measurement, the eye to be inspected is removed from the inspection position and then post-processing is executed. In the post-processing, the acquired tomographic images are checked and superimposing processing is executed. Alternatively, the processing returns to step S1, if necessary, to execute the measurement in a different mode.

In this manner, whether a micro saccade has occurred can be detected by analyzing the fundus image substantially in real time. This prevents the movement of the scanner to an unexpected position. As described above, the scanner is caused to track the eye movement and, at the same time, redundant photographing is eliminated, thereby increasing the probability of acquiring just required number of desired images.

Areas functioning as a coordinate value calculation unit, a spatial variation calculation unit, and a scan control unit in the PC 125 described above, respectively, execute the calculation of the coordinate values of the plurality of detection areas matching the plurality of previously-acquired characteristic areas, respectively, the calculation of the spatial variation between the plurality of calculated coordinate values, and the scan control of the measuring light, namely the tracking operation, which is executed to photograph a tomographic image of an eye to be inspected on the basis of the result of the calculation by the tomographic image photographing section in the fundus image described above.

Second Embodiment

This section describes only a difference from the first embodiment. The difference from the first embodiment is that the photographing of a fundus image by the SLO photographing section and the photographing of a tomographic image by the OCT photographing section are assumed to be executed independently of each other. In the case where the number of photographing frames is different between them, waste can be eliminated by photographing these images at different timings. Signal processing in this case is described with reference to a flowchart in FIG. 4. Although common processing is partially used in the flowchart of the fundus image and the tomographic image, it does not mean a coincidence of the temporal timing between them.

(Signal Processing)

Figure 4:
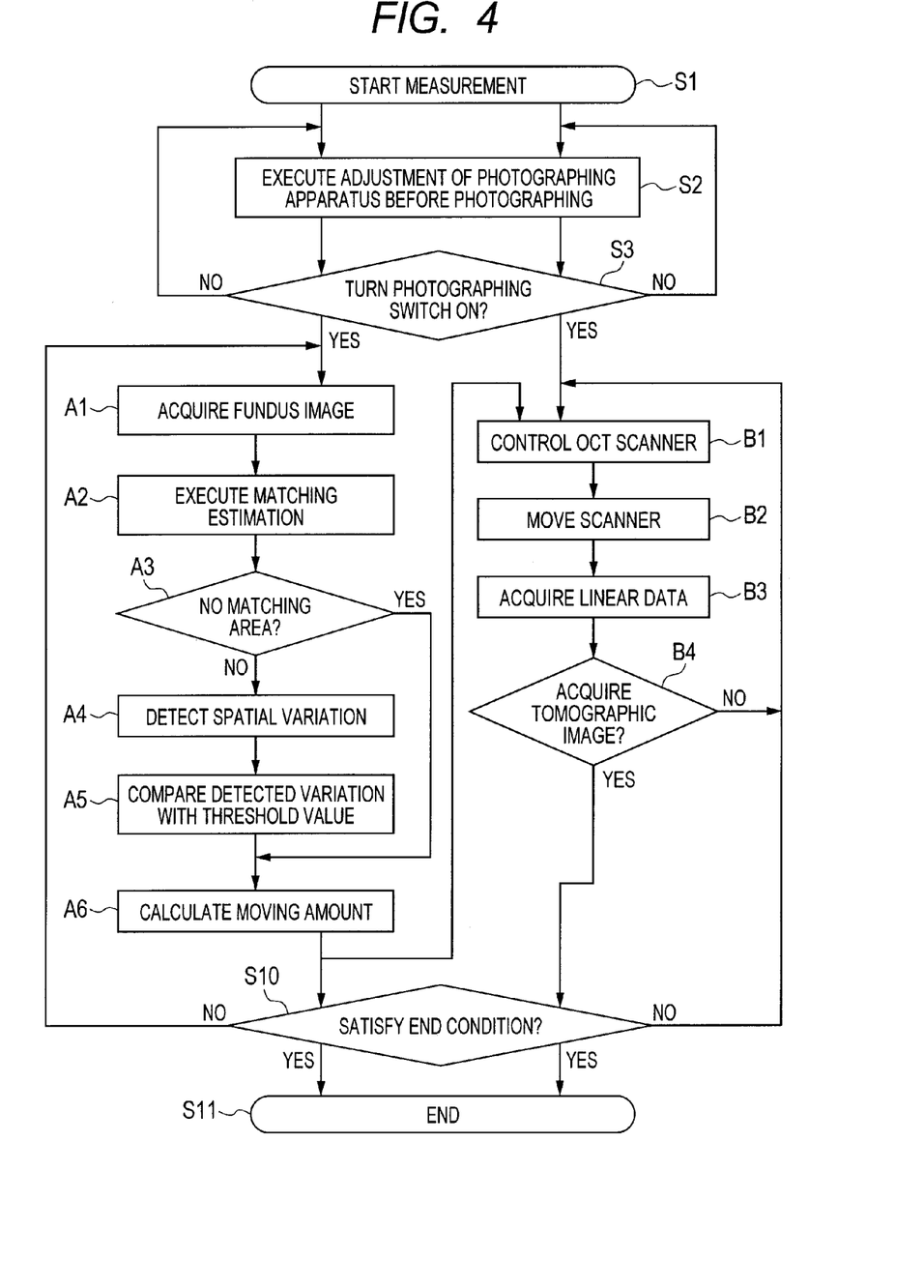
FIG. 4 is a flowchart of signal processing in a second embodiment of the present invention.

In step S1, the measurement is started. In this state, the photographing apparatus has already been started and an eye to be inspected has been disposed in the measurement position.

In step S2, the adjustment of the photographing apparatus before photographing is executed for the fundus image and the tomographic image. In this step, four templates are extracted.

In step S3, it is determined whether the photographing switch is turned on. If the photographing switch is turned on, the processing proceeds to step A1 for photographing the fundus image or to step B1 for photographing the tomographic image.

First, a photographing loop for the fundus image is described. It is assumed that the photographing of the fundus image takes 5 msec per frame.

In step A1, the fundus image is photographed. The fundus image is acquired by the SLO photographing section. The SLO scanner (X) 138 provides a fast scan and the SLO scanner (Y) 135 provides a slow scan, by which a two-dimensional fundus image in the xy plane is acquired. As a result, the acquired image has 800 pixels in the x direction and 600 pixels in the y direction.

In step A2, a matching estimation is executed between the fundus image and the templates. If there is no area matching the template, an error is output.

In step A3, it is determined whether there is no matching area. If there is no matching area as a result of the matching estimation, the processing proceeds to step A6. At this time, the OCT scanner is not controlled. Therefore, the current value is directly output as the moving amount. If there is a matching area, the processing proceeds to step A4.

In step A4, a spatial variation is detected. The spatial variation is detected from the matching detection areas according to the mathematical expressions 2 and 5.

In step A5, the detected spatial variation is compared with a threshold value. It is then estimated whether the mathematical expressions 6-1 and 6-2 are satisfied.

In step A6, the moving amount is calculated. If the spatial variation is smaller than the threshold value, the moving amount is calculated on the basis of the mathematical expression 8. If the spatial variation is greater than the threshold value, the current value is output as the moving amount without change.

Subsequently, the photographing loop for the tomographic image is described. It is assumed that the photographing by the OCT photographing section takes 25 msec per frame.

In step B1, the OCT scanner is controlled. The OCT scanner is controlled by referencing the calculation result of the moving amount in step A6. In the control of the OCT scanner, offsets both in the x and y directions are changed. In the case of acquiring data of 1,000 lines in the x direction, the control is updated per 200 lines.

In step B2, the OCT scanner is moved (accurately, an angle is changed). The OCT scanner is moved in the x direction by one step.

In step B3, linear data is acquired.

In step B4, it is determined whether the tomographic image is successfully acquired. If data of all lines are completed to be acquired, the processing proceeds to step B10. At this point, the acquired tomographic image has 1,000 pixels in the x direction and 500 pixels in the z direction. Unless the acquisition is completed, the processing returns to step B1.

In step S10, it is determined whether the acquisition of the desired number of images is completed. Unless the acquisition of the desired number of images is completed, the processing returns to step A1 for photographing the fundus image. On the other hand, the processing returns to step B1 for photographing the tomographic image. If the photographing of each image is completed or if the measurement time exceeds the specified time, the end processing is executed.

In step S11, the processing ends.

By analyzing the fundus image substantially in real time as described above, the scanner can be prevented from moving to an unexpected position. In addition, finer scanner control is achievable as long as the SLO photographing section acquires the fundus image sufficiently earlier than the acquisition of the tomographic image by the OCT photographing section.

Other Embodiment

Moreover, the present invention is realized by executing the following processing. Specifically, software (program)

for implementing the functions of the above embodiments is supplied to a system or an apparatus via a network or any of various storage media, and then a computer (or a CPU, an MPU, etc.) of the system or apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-052292, filed Mar. 10, 2011, which is hereby incorporated by reference herein in its entirety.

What is claimed is:

1. A control method of a photographing apparatus comprising the steps of:
acquiring first and second fundus images of an eye to be inspected at different times before or during OCT photographing;
extracting a plurality of characteristic images from the first fundus image acquired before or during OCT photographing;
searching, in the second fundus image acquired before or during OCT photographing, for a plurality of characteristic images corresponding to the plurality of characteristic images extracted from the first fundus image;
determining whether there is a spatial variation between (a) a positional relation of the plurality of characteristic images extracted from the first fundus image and (b) a positional relation of the plurality of characteristic images searched for in the second fundus image before or during OCT photographing; and
executing an eye tracking operation with an OCT photographing section before or during OCT photographing on the basis of the first and second fundus images acquired before or during OCT photographing in a case where the spatial variation satisfies a predetermined condition.

2. The control method of the photographing apparatus according to claim 1, further comprising the steps of:
acquiring a third fundus image of the eye to be inspected at a time different from those for the first and second fundus images in a case where the spatial variation does not satisfy the predetermined condition; and
executing the tracking operation on the basis of the first and third fundus images.

3. The control method of the photographing apparatus according to claim 1, wherein the extraction step includes extracting the plurality of characteristic images at three or more places in the first fundus image.

4. The control method of the photographing apparatus according to claim 1, further comprising the step of calculating, as the spatial variation, a variation (a) in a distance between characteristic images selected out of the plurality of characteristic images searched for in the second fundus image or (b) in an angle between two line segments connecting the plurality of characteristic images searched for in the second fundus image.

5. The control method of the photographing apparatus according to claim 1, wherein:
the extraction step includes extracting the plurality of characteristic images at four or more places in the first fundus image; and further comprising the step of calculating, as the spatial variation, a variation in a distance between at least one pair of the characteristic images searched for in the second fundus image.

6. The control method of the photographing apparatus according to claim 1, wherein the plurality of characteristic images extracted from the first fundus image exist at four or more places, and
further comprising the step of calculating, as the spatial variation, a variation in an angle between two diagonal lines connecting the plurality of characteristic images searched for in the second fundus image which are diagonally opposite to each other in the fundus image and have been searched.

7. The control method of the photographing apparatus according to claim 1, further comprising the step of calculating, as the spatial variation, a movement of a centroid of the characteristic images searched for in the second fundus image relative to a centroid of the characteristic images extracted from the first fundus image.

8. The control method of the photographing apparatus according to claim 1, further comprising the step of controlling a scan mode for scanning the eye to be inspected using a measuring light for use in acquiring a tomographic image of the eye to be inspected.

9. The control method of the photographing apparatus according to claim 1, wherein, in a case where the spatial variation is greater than a predetermined value, a tomographic image is discarded, where the tomographic image is acquired at the same time as the fundus image when acquiring the characteristic image searched for in the second fundus image used to detect matching with the characteristic image extracted from the first fundus image.

10. A recording medium for recording a program which causes a computer to execute the respective steps of the control method of the photographing apparatus according to claim 1.

11. A photographing apparatus comprising:
an acquiring unit configured to acquire first and second fundus images of an eye to be inspected at different times before or during OCT photographing;
an extraction unit configured to extract a plurality of characteristic images from the first fundus image acquired before or during OCT photographing;
a search unit configured to search, in the second fundus image acquired before or during OCT photographing, for a plurality of characteristic images corresponding to the plurality of characteristic images extracted from the first fundus image;
a determination unit configured to determine whether there is a spatial variation between (a) a positional relation of the plurality of characteristic images extracted from the first fundus image and (b) a positional relation of the plurality of characteristic images searched for in the second fundus image before or during OCT photographing; and
a scan control unit of an OCT photographing section configured to execute an eye tracking operation before or during OCT photographing on the basis of the first and second fundus images acquired before or during OCT photographing in a case where the spatial variation satisfies a predetermined condition.

12. The photographing apparatus according to claim 11, wherein:
the acquiring unit acquires a third fundus image of the eye to be inspected at a time different from those for the first and second fundus images in a case where the spatial variation does not satisfy the predetermined condition; and the scan control unit executes the tracking operation on the basis of the first and third fundus images.

13. A photographing method comprising the steps of:
acquiring first and second fundus images of an eye to be inspected at different times before or during OCT photographing;
extracting a plurality of characteristic images from the first fundus image acquired before or during OCT photographing;
searching, in the second fundus image acquired before or during OCT photographing, for a plurality of characteristic images corresponding to the plurality of characteristic images extracted from the first fundus image; and
executing an eye a tracking operation with an OCT photographing section before or during OCT photographing using a difference between (a) a positional relation of the plurality of characteristic images extracted from the first fundus image acquired before or during OCT photographing and (b) a positional relation of the plurality of characteristic images searched for in the second fundus image acquired before or during OCT photographing.

14. A photographing method according to claim 13, wherein in the step of executing the tracking operation, the tracking operation is executed, in a case where the difference satisfies a predetermined condition, based on the first fundus image and the second fundus image, and
wherein the tracking operation is executed, in a case where the difference does not satisfy the predetermined condition, based on the first fundus image and a third fundus image which is acquired at a time different from those for the first and second fundus images.

15. A recording medium for recording a program which causes a computer to execute the respective steps of the photographing method according to claim 13.

16. A photographing apparatus comprising:
an acquiring unit configured to acquire first and second fundus images of an eye to be inspected at different times before or during OCT photographing;
an extracting unit configured to extract a plurality of characteristic images from the first fundus image acquired before or during OCT photographing;
a searching unit configured to search, in the second fundus image acquired before or during OCT photographing, for a plurality of characteristic images corresponding to the plurality of characteristic images extracted from the first fundus image; and
a tracking unit configured to execute an eye tracking operation of an OCT photographing section before or during OCT photographing using a difference between (a) a positional relation of the plurality of characteristic images extracted from the first fundus image acquired before or during OCT photographing and (b) a positional relation of the plurality of characteristic images searched for in the second fundus image acquired before or during OCT photographing.

17. A photographing apparatus according to claim 16, wherein the tracking unit executes the tracking operation, in a case where the difference satisfies a predetermined condition, based on the first fundus image and the second fundus image, and
wherein the tracking unit executes the tracking operation, in a case where the difference does not satisfy the predetermined condition, based on the first fundus image and a third fundus image which is acquired at a time different from those for the first and second fundus images.

18. The control method of the photographing apparatus according to claim 1, wherein in a case that the spatial variation is less than a predetermined value, the spatial variation satisfies the predetermined condition.

19. The photographing apparatus according to claim 11, wherein in a case that the spatial variation is less than a predetermined value, the spatial variation satisfies the predetermined condition.

20. The control method of the photographing apparatus according to claim 2, wherein in a case that the spatial variation is equal to or greater than a predetermined value, the spatial variation does not satisfy the predetermined condition.

21. The photographing apparatus according to claim 12, wherein in a case that the spatial variation is equal to or greater than a predetermined value, the spatial variation does not satisfy the predetermined condition.

22. The control method of the photographing apparatus according to claim 14,
wherein in a case that the difference is less than a threshold value, the difference satisfies the predetermined condition, and
wherein in a case that the difference is equal to or greater than the threshold value, the difference does not satisfy the predetermined condition.

23. The photographing apparatus according to claim 17,
wherein in a case that the difference is less than a threshold value, the difference satisfies the predetermined condition, and
wherein in a case that the difference is equal to or greater than the threshold value, the difference does not satisfy the predetermined condition.

24. A photographing apparatus comprising:
an acquiring unit configured to acquire first and second fundus images of an eye to be inspected at different times before or during OCT photographing;
an extracting unit configured to extract a plurality of characteristic images from the first fundus image acquired before or during OCT photographing;
a searching unit configured to search, in the second fundus image acquired before or during OCT photographing, for a plurality of characteristic images corresponding to the plurality of characteristic images extracted from the first fundus image; and
a determining unit configured to determine, based on a searching result of the searching unit, that an eye tracking operation of an OCT photographing section before or during OCT photographing is not executed, the eye tracking operation being executed by using the second fundus image acquired before or during OCT photographing.

25. A photographing method comprising the steps of:
acquiring first and second fundus images of an eye to be inspected at different times before or during OCT photographing;
extracting a plurality of characteristic images from the first fundus image acquired before or during OCT photographing;
searching, in the second fundus image acquired before or during OCT photographing, for a plurality of characteristic images corresponding to the plurality of characteristic images extracted from the first fundus image; and
determining, based on a searching result in the step of searching, that an eye tracking operation of an OCT photographing section before or during OCT photographing is not executed, the eye tracking operation being executed by using the second fundus image acquired before or during OCT photographing.

26. A recording medium for recording a program that causes a computer to execute the respective steps of the photographing method according to claim 25.

27. A photographing apparatus according to claim 24,
further comprising a tracking unit configured to execute the tracking operation, in a case where the searching result satisfies a predetermined condition, based on the first fundus image and the second fundus image, and
wherein the tracking unit executes the tracking operation, in a case where the searching result does not satisfy the predetermined condition, based on the first fundus image and a third fundus image which is acquired at a time different from those for the first and second fundus images.

28. A photographing method according to claim 25,
wherein the tracking operation is executed, in a case where the searching result satisfies a predetermined condition, based on the first fundus image and the second fundus image, and
wherein the tracking operation is executed, in a case where the searching result does not satisfy the predetermined condition, based on the first fundus image and a third fundus image which is acquired at a time different from those for the first and second fundus images.

29. The photographing apparatus according to claim 27,
wherein in a case that a value designating the searching result is less than a predetermined threshold value, the searching result satisfies the predetermined condition, and
wherein in a case that the value designating the searching result is equal to or greater than the predetermined threshold value, the searching result does not satisfy the predetermined condition.

30. The control method of the photographing apparatus according to claim 28,
wherein in a case that a value designating the searching result is less than a predetermined threshold value, the searching result satisfies the predetermined condition, and
wherein in a case that the value designating the searching result is equal to or greater than the predetermined threshold value, the searching result does not satisfy the predetermined condition.

31. A control method of a photographing apparatus having an OCT photographing section having an OCT scanner and performing OCT photographing and a fundus-image-obtaining section obtaining and analyzing fundus images, the method comprising the steps of:
operating the OCT photographing section and the fundus-image-obtaining section to perform OCT photographing and fundus-image photographing independently of each other;
operating the fundus-image-obtaining section to:
acquire first and second fundus images of an eye to be inspected at different times;
extracting a plurality of characteristic images from the first fundus image acquired;
searching, in the second fundus image for a plurality of characteristic images corresponding to the plurality of characteristic images extracted from the first fundus image;
determining whether there is a spatial variation between (a) a positional relation of the plurality of characteristic images extracted from the first fundus image and (b) a positional relation of the plurality of characteristic images searched for in the second fundus image; and
operating the OCT photographing section to control the OCT scanner during OCT photographing of on the basis of the first and second fundus images acquired before the completion of OCT photographing in a case where the spatial variation satisfies a predetermined condition.

32. A recording medium for recording a program which causes a computer to execute the respective steps of the control method of the photographing apparatus according to claim 31.

* * * * *